(12) United States Patent
Bäck et al.

(10) Patent No.: US 10,258,515 B2
(45) Date of Patent: Apr. 16, 2019

(54) ABSORBENT ARTICLE IN THE FORM OF BOXER SHORTS AND METHOD FOR MAKING THEREOF

(75) Inventors: Lucas Bäck, Billdal (SE); Tony Karlsson, Sävedalen (SE); Lennart Nilsson, Skärhamn (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 1260 days.

(21) Appl. No.: 13/994,970

(22) PCT Filed: Dec. 20, 2010

(86) PCT No.: PCT/SE2010/051438
§ 371 (c)(1),
(2), (4) Date: Jun. 17, 2013

(87) PCT Pub. No.: WO2012/087196
PCT Pub. Date: Jun. 28, 2012

(65) Prior Publication Data
US 2013/0281958 A1 Oct. 24, 2013

(51) Int. Cl.
*A61F 13/15* (2006.01)
*A61F 13/49* (2006.01)
*A61F 13/496* (2006.01)

(52) U.S. Cl.
CPC .. *A61F 13/49017* (2013.01); *A61F 13/15699* (2013.01); *A61F 13/15739* (2013.01);
(Continued)

(58) Field of Classification Search
CPC .......... A61F 13/49033; A61F 13/49022; A61F 13/49023; A61F 13/15699;
(Continued)

(56) References Cited

U.S. PATENT DOCUMENTS

| 2,366,865 | A | 1/1945 | Messing |
| 4,427,408 | A | 1/1984 | Karami et al. |

(Continued)

FOREIGN PATENT DOCUMENTS

| EP | 1 035 818 | 9/2000 |
| EP | 1 793 780 B1 | 6/2007 |

(Continued)

OTHER PUBLICATIONS

The extended European Search Report dated Jul. 15, 2014, by the European Patent Office in corresponding European Patent Application No. 10861133.6-1308. (5 pages).

(Continued)

*Primary Examiner* — Bradley H Philips
(74) *Attorney, Agent, or Firm* — Buchanan Ingersoll & Rooney P.C.

(57) ABSTRACT

An absorbent pant article in the form of boxer shorts includes a garment shell including a front body panel, a back body panel and a crotch panel made of elastic web material. The pant also includes an absorbent core, side seams connecting the front body panel to the back body panel, a pair of leg openings and hanging legs. The leg openings are located in the crotch panel and do not extend into the front and back body panels, and side seams extend into the crotch panel. The width of the crotch panel in a relaxed condition of the elastic web material, as measured between the side seams of the article, is at least 7% larger than the width of any of the front and back body panels in a relaxed condition of the respective elastic web material.

14 Claims, 6 Drawing Sheets

(52) U.S. Cl.
 CPC ...... *A61F 13/15804* (2013.01); *A61F 13/496* (2013.01); *A61F 13/49012* (2013.01); *A61F 13/49015* (2013.01); *A61F 2013/49038* (2013.01); *Y10T 156/1002* (2015.01)

(58) Field of Classification Search
 CPC .......... A61F 13/49012; A61F 13/49017; A61F 13/496; A61F 13/4963; A61F 13/49038; A61F 13/49039; A61F 13/4906; A61F 13/49046; A61F 13/49095; A61F 13/49088; A61F 13/4915; Y10T 156/1002; A41B 9/02; A41B 9/023; A41B 9/026
 See application file for complete search history.

(56) References Cited

U.S. PATENT DOCUMENTS

| | | | |
|---|---|---|---|
| 4,743,241 A * | 5/1988 | Igaue et al. | 604/385.26 |
| D315,050 S | 3/1991 | Bush et al. | |
| 5,669,902 A | 9/1997 | Sivilich | |
| 6,964,238 B2 | 11/2005 | Mortell et al. | |
| 7,198,688 B2 | 4/2007 | Mortell et al. | |
| 7,632,259 B2 * | 12/2009 | Elfstrom et al. | 604/385.27 |
| 2003/0115660 A1 | 6/2003 | Hopkins | |
| 2004/0107481 A1 | 6/2004 | Mortell et al. | |
| 2005/0120465 A1 | 6/2005 | Franke et al. | |
| 2005/0120466 A1* | 6/2005 | Coenen et al. | 2/400 |
| 2005/0124948 A1 | 6/2005 | Morman et al. | |
| 2008/0236735 A1 | 10/2008 | Kurata | |
| 2009/0008023 A1 | 1/2009 | Verhaert et al. | |
| 2010/0262103 A1* | 10/2010 | Turner et al. | 604/365 |

FOREIGN PATENT DOCUMENTS

| | | |
|---|---|---|
| GB | 2 112 268 A | 7/1983 |
| JP | 2006-509116 A | 3/2006 |
| WO | WO 03/047488 A1 | 6/2003 |
| WO | 2004/062398 A1 | 7/2004 |
| WO | WO 2005/122985 A1 | 12/2005 |

OTHER PUBLICATIONS

An English Translation of the Office Action (Decision on Grant) dated Nov. 14, 2014, by the Russian Patent Office in corresponding Russian Patent Application No. 2013134164. (6 pages).

Office Action (Notice of Reasons for Rejection) dated Jan. 13, 2015, by the Japanese Patent Office in corresponding Japanese Patent Application No. 2013-546068, with an English translation of the Office Action. (5 pages).

International Search Report (PCT/ISA/210) dated Sep. 12, 2011, by the Swedish Patent Office as the International Searching Authority for International Application No. PCT/SE2010/051438.

Written Opinion (PCT/ISA/237) dated Sep. 12, 2011, by the Swedish Patent Office as the International Searching Authority for International Application No. PCT/SE2010/051438.

International Preliminary Report on Patentability (PCT/IPEA/409) dated Oct. 11, 2012, by the Swedish Patent Office as the International Searching Authority for International Application No. PCT/SE2010/051438.

* cited by examiner

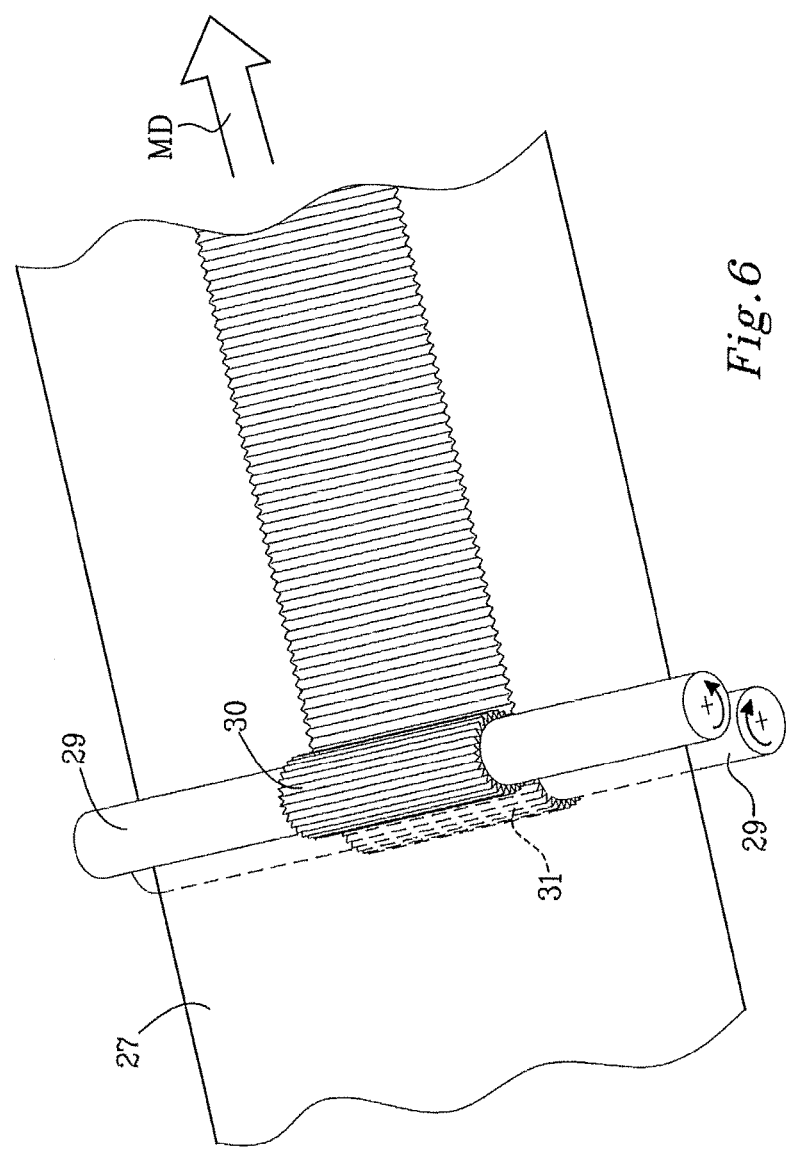

ABSORBENT ARTICLE IN THE FORM OF BOXER SHORTS AND METHOD FOR MAKING THEREOF

TECHNICAL FIELD

The present invention relates to absorbent articles in the form of boxer shorts comprising a garment shell including a front body panel, a back body panel, a crotch panel positioned between the front and back body panels, an absorbent core arranged in at least the crotch panel, a front waist edge, a back waist edge, side seams connecting the front body panel to the back body panel, a pair of leg openings and hanging legs. The invention further relates to methods of making absorbent articles in the form of boxer shorts.

BACKGROUND

Absorbent pant articles like pant diapers, sanitary pants and incontinence pants have a comfortable fit and are capable of being pulled up and down over the hips of the wearer to allow the wearer or caregiver to easily put on and remove the article when it has been soiled. Absorbent pant articles in the form of boxer shorts resemble conventional underwear and are preferred by many users. However disposable absorbent boxer shorts present manufacturing challenges and product design is often compromised by cost and manufacturing aspects. This is in part due to the fact that a high manufacturing speed is necessary to be able to produce low-cost disposable absorbent articles.

U.S. Pat. No. 7,198,688 discloses a process for making boxer shorts, for example in the form of disposable absorbent articles. The garment shell of the boxer shorts is provided from a flat web having leg openings therein. The flat web is contracted in the crotch region to provide hanging legs and side seams are formed to create a boxer shorts type pant.

EP 1793780 discloses boxer shorts and a process for making them. The crotch region and/or the back region comprise an expandable material in the form of a separate piece of material attached to the garment shell web in the front and/or back region thereof.

There is however still a need for improvement of the product design of boxer shorts type absorbent articles especially with respect to the creation of comfort and fit in the leg openings and the hanging legs.

SUMMARY

One object of the present disclosure is to provide a solution to the above problem, wherein according to the present disclosure each of said front body panel, back body panel and crotch panel is made of elastic web material, the leg openings are located in the crotch panel and do not extend into the front and back body panels, and said side seams extend into the crotch panel, and that the width of the crotch panel in a relaxed condition of the elastic web material, as measured between the side seams of the article, is at least 7% larger than the width of any of the front and back body panels in a relaxed condition of the respective elastic web material, as measured between the side seams of the article.

The width of the crotch panel in a relaxed condition of the elastic web material, as measured between the side seams of the article may be at least 10% larger than the width of any of the front and back body panels in a relaxed condition of the respective elastic web material, as measured between the side seams of the article.

The width of the crotch panel in a relaxed condition of the elastic web material, as measured between the side seams of the article may be not more than 100%, preferably between 10 and 70% and more preferably between 20 and 40%, larger than the width of any of the front and back body panels in a relaxed condition of the respective elastic web material, as measured between the side seams of the article.

The elastic web material in the crotch panel may be a separate elastic web material attached to the elastic web material of the front and back body panels.

The elastic web material in the crotch panel may be joined to the elastic web material in said at least one of the front and back body panels while at least the elastic web material of said at least one of the front and back body panels being held in an elongated condition, and the elastic web material in the crotch panel being in a relaxed condition or in a less elongated condition as compared to the elastic web material in said at least one of the front and back body panels.

The elastic web material in the crotch panel may be of the same type as the elastic web material in at least one of the front and back body panels.

The elastic web material in the crotch panel may be of a different type than the elastic web material in at least one of the front and back body panels.

The elastic web material in the crotch panel may be the same and integral with the elastic web material in the front and back body panels, and has been exerted to a treatment that has extended or deformed the elastic web material in the crotch panel in the transverse direction of the pant article so that the width of the crotch panel will be larger than the width of any of the front and back body panels.

Said side seams may extend at least 10 mm, preferably at least 20 mm, into the crotch panel.

The elastic web material in the front, back and crotch panels may be an elastic laminate comprising at least one fibrous layer and at least one film layer.

The present disclosure further refers to a method of making an absorbent pant article in the form of boxer shorts, said boxer shorts comprising a garment shell including a front body panel, a back body panel, a crotch panel positioned between the front and back body panels, an absorbent core arranged in at least the crotch panel, a front waist edge, a back waist edge, side seams connecting the front body panel to the back body panel, a pair of leg openings and hanging legs, wherein said method comprises the steps of: providing an elastic web material intended to form said crotch panel, providing elastic web materials intended to form said front and back body panels, attaching the crotch panel web material to each of the front and back panel web materials, at least one of elastic web materials forming the front and back body panels being held in an elongated condition, and the elastic web material forming crotch panel being in a relaxed condition or in a less elongated condition as compared to the elastic web material forming said at least one of the front and back body panels when being attached to each other, providing leg openings in the crotch panel web material, attaching an absorbent core to at least the crotch panel web material, attaching the front and back panel web materials together to form said side seams, said side seams extending into the crotch panel web material.

The crotch panel web material may be of the same or of different type as said at least one of the front and back panel web materials.

The present disclosure further refers to a method of making an absorbent pant article in the form of boxer shorts, said boxer shorts may comprise a garment shell including a front body panel, a back body panel, a crotch panel positioned between the front and back body panels, an absorbent core arranged in at least the crotch panel, a front waist edge, a back waist edge, side seams connecting the front body panel to the back body panel, a pair of leg openings and hanging legs, wherein said method comprises the steps of: providing an elastic web material intended to form said front, back and crotch panels, exerting the elastic web material in the area intended to form the crotch panel to a treatment that will extend the elastic web material in a direction intended to form the transverse (x) direction of the absorbent pant, so that the elastic web material in the area intended to form the crotch panel will have a dimension exceeding the dimension of the elastic web material in the areas intended to form the front and back body panels, providing leg openings in the crotch panel area, attaching an absorbent core to at least the crotch panel area, attaching the front and back panel areas together to form said side seams, said side seams extending into the crotch panel area.

BRIEF DESCRIPTION OF THE DRAWINGS

FIGS. 5A, 5B and FIG. 6 illustrate schematically two different processes for making the boxer shorts.

DETAILED DESCRIPTION OF PREFERRED EMBODIMENTS

Embodiments of the invention will in the following be closer described with reference to some embodiments shown in the accompanying drawings.

Figure 1:
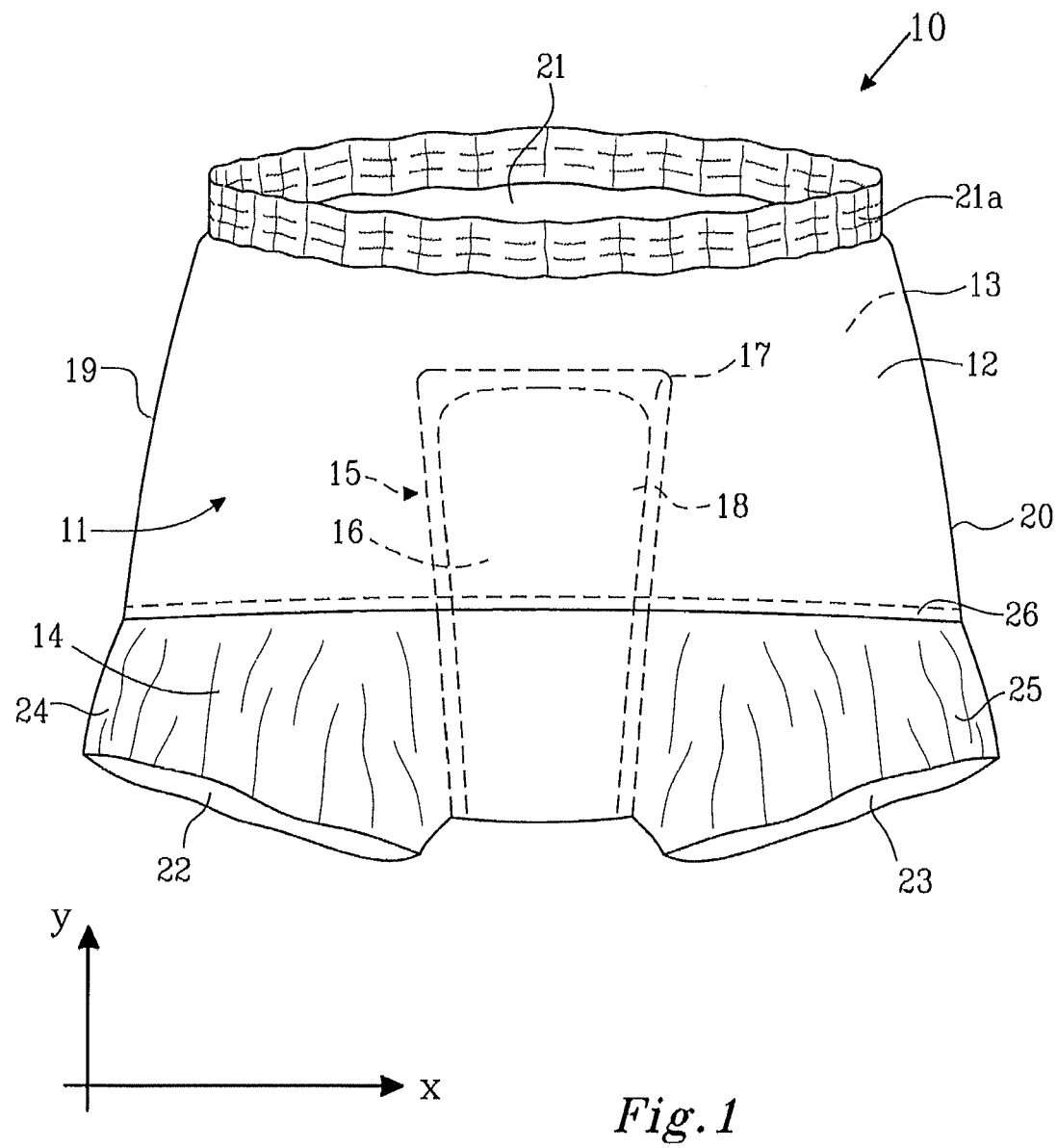
FIG. 1 is a front view of an embodiment of a pair of boxer shorts according to the present disclosure.

FIG. 1 shows an embodiment of an absorbent pant 10 in the form of boxer shorts. The term "absorbent pant" refers to a pant product that is placed against the skin of the wearer to absorb and contain body exudates, like urine, fæces and menstrual fluid. The present disclosure mainly refers to disposable absorbent pants, which means an article that is not intended to be laundered or otherwise restored or reused as an absorbent pant after use. Pant-type absorbent articles in the form of boxer shorts are referred to. "Boxer shorts" refers to a pant having hanging legs. They may have numerous applications such as pant diapers, feminine care pants, incontinence pants, disposable swimwear and the like.

The pant comprises a garment shell 11 including a front body panel 12, a back body panel 13 and a crotch panel 14 positioned between the front and back body panels. The front and back panels 12 and 13 are joined together at side seams 19 and 20 to define a three-dimensional pant configuration having a waist opening 21 and a pair of leg openings 22 and 23 with hanging legs 24 and 25. The side seams may be formed in any conventional manner, like ultrasonic welding, thermobonding, gluing or the like.

The leg openings 22 and 23 are formed in the crotch panel 14 and do not extend into the front and back body panels 12 and 13. The side seams 19 and 20 extend into the crotch panel 14, which form the hanging legs 24 and 25. Preferably the side seams 19 and 20 extend at least 10 mm, preferably at least 20 mm, into the crotch panel.

Figure 2A:
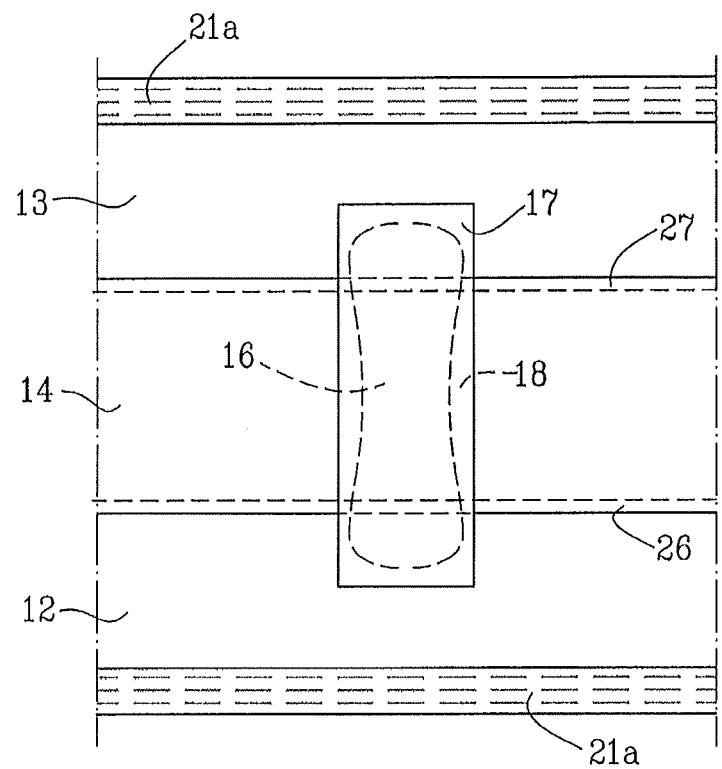
FIG. 2A is a plan view of an assembled garment shell web according to a first embodiment having an absorbent assembly attached thereto.
Figure 2B:
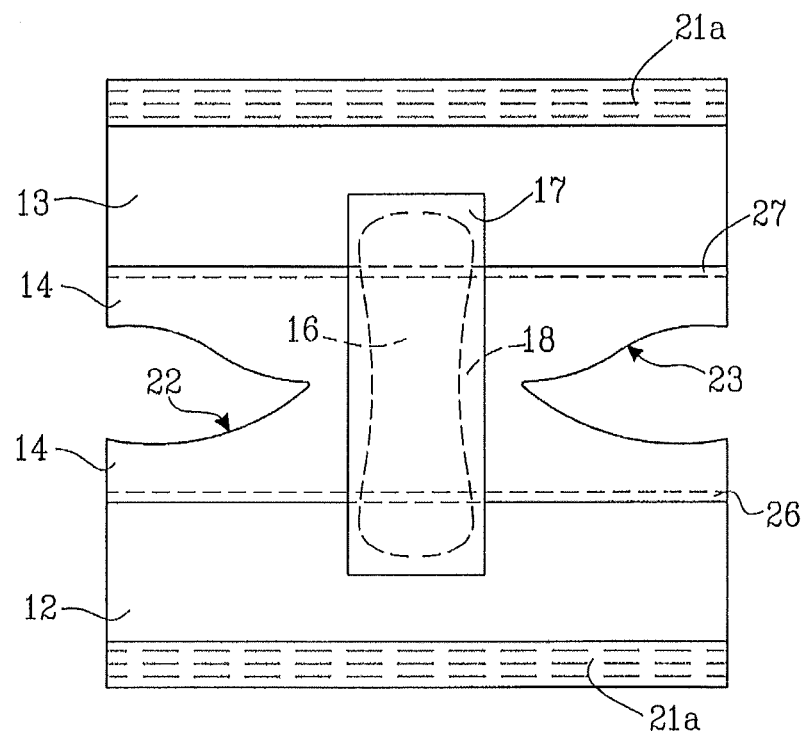
FIG. 2B shows the assembled garment shell web having leg cuts made therein.
Figure 3:
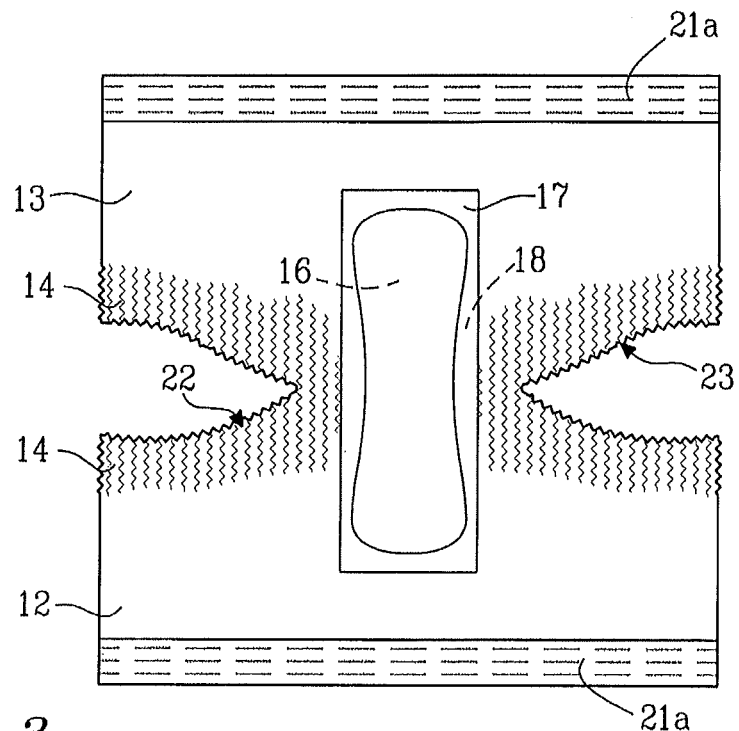
FIG. 3 is a plan view of an assembled garment shell web according to a second embodiment having an absorbent assembly attached thereto.

The front body panel 12, back body panel 13 and crotch panel 14 are made of elastic web material, which will be described more in detail below. The crotch panel 14 may be a separate elastic web material attached to the elastic web material of the front and back body panels 13 and 14 along seams 26 and 27, as illustrated in FIGS. 1 and 2A,B for example. The seams 26 and 27 may be formed in any conventional manner, like ultrasonic welding, thermobonding, gluing or the like. Alternatively the crotch panel 14 is integral with the front and back body panels 12 and 13, as illustrated in FIG. 3.

A core region 15 comprising an absorbent core 16 is located in the crotch panel 14 and extends into the front 12 and back panels 13. The absorbent core 16 is enclosed between a liquid permeable topsheet 17 and a liquid impermeable backsheet 18.

The pant 10 may further comprise an elastic waistband 21a. The waistband 21a may comprise a nonwoven material that is elasticized by elastic members 14, such as elastic threads, contractably affixed between material layers, such as nonwoven materials. The waistband 21a is joined to the waist edges of the front and back panels 12 and 13 in any conventional manner, like ultrasonic welding, thermobonding, gluing or the like.

The pant has a longitudinal direction y and a transverse direction x.

Below a description will be given of the different components of the pant.

Topsheet

The liquid permeable topsheet 17 can consist of a nonwoven material, e g spunbond, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or from a mixture of natural and manmade fibres. The topsheet material may further be composed of tow fibres, which may be bonded to each other in a bonding pattern, as e.g. disclosed in EP-A-1 035 818. Further examples of topsheet materials are porous foams, apertured plastic films etc. The materials suited as topsheet materials should be soft and non-irritating to the skin and intended to be readily penetrated by body fluid, e.g. urine or menstrual fluid. The topsheet may be different in different parts of the absorbent article.

Backsheet

The liquid impervious backsheet 18 is of a liquid impervious material, such as a thin plastic film, e.g. a polyethylene or polypropylene film, a nonwoven material coated with a liquid impervious material, a hydrophobic nonwoven material, which resists liquid penetration or a laminate comprising plastic films and nonwoven materials. The liquid impervious backsheet material 18 may be breathable so as to allow vapour to escape from the absorbent core, while still preventing liquids from passing therethrough. Examples of breathable backsheet materials are porous polymeric films, nonwoven laminates from spunbond and meltblown layers, laminates from porous polymeric films and nonwovens. The backsheet material 18 is preferably inelastic.

Absorbent Core

The absorbent core 16 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times its weight and in an aqueous solution containing 0.9 weight percent of sodium chloride. Organic materials suitable for use as a superabsorbent material can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble. Preferred superabsorbent materials are further surface crosslinked so that the outer surface or shell of the superabsorbent particle, fiber, flake, sphere, etc. possesses a higher crosslink density than the inner portion of the superabsorbent. The superabsorbent materials may be in any form suitable for use in absorbent composites including particles, fibers, flakes, spheres, and the like.

A high absorption capacity is provided by the use of high amounts of superabsorbent material. For an absorbent core comprising a matrix of hydrophilic fibers, such as cellulosic fibers, and superabsorbent material, the proportion of superabsorbent material is preferably between 10 and 90% by weight, more preferably between 30 and 70% by weight.

It is conventional in absorbent articles to have absorbent cores comprising layers of different properties with respect to liquid receiving capacity, liquid distribution capacity and storage capacity. The thin absorbent bodies, which are common in for example baby diapers and incontinence guards, often comprise a compressed mixed or layered structure of cellulosic fluff pulp and superabsorbent polymers. The size and absorbent capacity of the absorbent core may be varied to be suited for different uses such as for infants or for adult incontinent persons.

The absorbent core may further include an acquisition distribution layer placed on top of the primary absorbent body and which is adapted to quickly receive and temporarily store discharged liquid before it is absorbed by the primary absorbent core. Such acquisition distribution layers are well known in the art and may be composed of porous fibrous waddings or foam materials.

Elastic Web Material

The front and back body panels 12 and 13 as well as the crotch panel 14 of the garment shell 11 comprise an elastic web material, which is elastic at least in the transverse x-direction of the article. The elasticity in the x-direction should be at least 30%, preferably at least 50%, more preferably at least 70%, as measured by the Elasticity test specified below.

The elastic laminate material may also be elastic in the y-direction of the article. However the elasticity in the y-direction is preferably lower than in the x-direction.

The elastic web material may be an elastic laminate material. Such an elastic laminate may be composed of at least two web-shaped material layers in the form of nonwoven layers and/or film layers. At least one of the web-shaped layers in the laminate is elastic. Alternatively the elastic laminate material may comprise a plurality of elongated elastic members, such as elastic threads or strips, which are contractably affixed in an extended state between web-shaped materials, for example nonwoven materials. In the embodiment shown and described below the elastic laminate is composed of first and second outer layers of fibrous material and a middle elastic film layer located between said fibrous layers.

The outer fibrous layers should provide a soft and cloth-like feel to the laminate. Examples of suitable materials used as outer fibrous layers are carded webs, spunbond materials and creped or creased nonwovens. The basis weight of the fibrous material layers should be between 10 and 35 $g/m^2$, preferably between 12 and 30 $g/m^2$, more preferably between 15 and 25 $g/m^2$. Examples of suitable polymers used in the fibrous materials are polyethylene, polyesters, polypropylene and other polyolefin homopolymers and copolymers. Natural fibres, for example cotton, may also be used as long as they provide the required properties. A mixture of polymers can contribute to a higher flexibility of the nonwoven layer, and through this, give the nonwoven material a higher elongation at maximum load. A mixture of polyethylene and polypropylene polymers has proved to provide good results in this respect. A mixture of fibers of different polymers is also possible. Conjugate fibers may also be used, in which two or more polymers are arranged in positioned distinct zones across the cross-section of the conjugate fibers. Conjugate fibers are also referred to a bicomponent or multicomponent fibers.

The middle layer may according to one embodiment of the invention be an apertured elastic film having a basis weight between 20 and 80 $g/m^2$, preferably between 20 and 60 $g/m^2$. The film may be of any suitable elastic polymer, natural or synthetic. Some examples of suitable materials for the elastic film are low crystallinity polyethylenes, metallocene-catalyzed low crystallinity polyethylene, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. One example of a suitable film is an apertured three-layer elastomeric film of PE-SEBS-PE.

The total basis weight of the laminate is preferably 120 $g/m^2$ or less, preferably no more than 110 $g/m^2$ and more preferably no more than 100 $g/m^2$.

One example of an elastic laminate is manufactured according to the method disclosed in WO 03/047488, wherein one spunbond layer is applied to the film in a tacky state and will thus bond to the film layer, while the other spunbond layer is adhesively laminated to the film layer, using for example a pressure sensitive hot melt adhesive. Alternatively the laminate is manufactured according to a modified version of this known method, wherein the modification involves that the laminate is incrementally stretched (through intermeshing gears, IMG), to a point below the elongation at peak load of at least one of the non-elastic nonwoven layers to retain some strength for at least one of the nonwoven layers. The other layer may also be stretched to a point below its elongation at peak load, or to a point at which it will tear during stretching.

The method disclosed in WO 03/047488 involves stretching of the laminate above the point of failure of the fibrous material, so that the non-elastic layers break completely. Therefore, as described in WO 03/047488, the elongation of the laminate is not limited by the stretch modulus of the non-elastic material.

According to the modified method at least one, preferably both fibrous layers, which are bonded to the elastic film are not, in contrast to the method described in WO 03/047488, completely torn upon manufacture of a laminate according to the present disclosure. Selection of fibrous materials which have an elongation at maximum load greater than the elasticity of the elastic laminate allows the elastic film to stretch without being hindered by the fibrous layers. Such a selection also ensures that the fibrous layers contribute to the puncture resistance of the laminate, as they are not completely torn or broken during manufacture. Preferably the fibrous layers, or at least one of the fibrous layers have an elongation at maximum load that is at least 10% higher than the elasticity of the laminate. This is described in more detail in WO2005/122985.

In an alternative embodiment the laminate is manufacture by feeding a first fibrous layer in the form of a nonwoven web into a bonding nip and extruding a molten elastic film-forming polymer through a die into the nip. The first fibrous layer and the elastic film form a first laminate. In a second lamination step the film side of the first laminate is coated or sprayed with adhesive and is subsequently passed through a second bonding nip together with a second fibrous layer to form the laminate. The laminate is subsequently activated by subjecting it to incremental stretching by passing it through intermeshing gears, IMG.

In a further embodiment the first layer of fibrous material and the elastic film layer form parts of a first elastic laminate that has been rendered elastic by incremental stretching and partial tearing of the first layer of fibrous material and in which the first elastic laminate has been bonded to the second layer of fibrous material while in a stretched state. The resulting the laminate will then be elastically stretchable.

In a still further embodiment the first and second layers of fibrous material have been bonded to the elastic film layer while this is in a stretched state. The resulting laminate will be elastically stretchable.

It is further preferred that the elastic laminate 11 has a breathability (Water Vapour Transmission Rate) according to ASTM E96-00 Procedure D of at least 1500 g/m$^2$ 24 h, preferably at least 3000 g/m$^2$ 24 h.

Embodiments of Boxer Shorts

Figure 4:
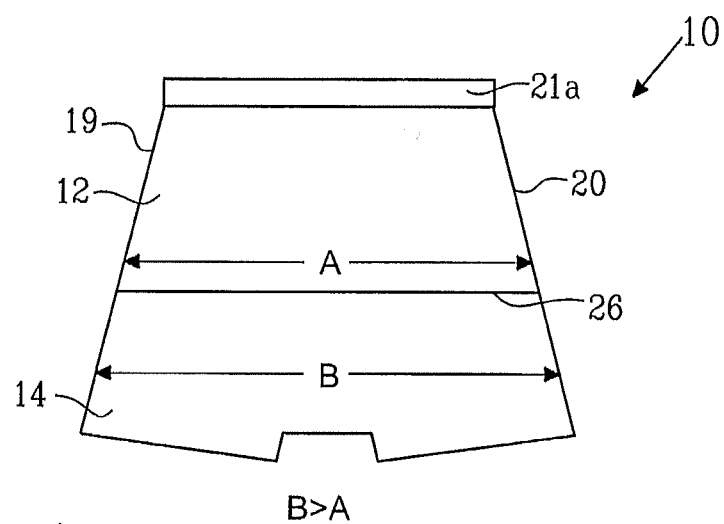
FIG. 4 illustrates schematically a pair of boxer shorts having the dimensions claimed.

The boxer pants according to the present disclosure has a greater width, as seen in the transverse direction x, in the crotch panel area 14 than in the front 12 and back 13 body panel areas in a relaxed condition of the elastic web material. This will ensure the fit and comfort in the leg opening area, which normally requires a higher width than for example in the waist area. The width A and B is as illustrated in FIG. 4 measured as the distance between the side seams 19 and 20 of the pant article when measured in a relaxed condition of the respective elastic web material. The width between the side seams 19 and 20 in the crotch panel is at least 7% larger than the width of any of the front and back body panels. Normally, the width of the front and back body panels are substantially the same. However if width of the front and back body panels would not be the same, the width of the crotch panel area should be at least 7% larger than the width of the widest of the front and back body panels.

The width of the crotch panel may be at least 10% larger than the width of any of the front and back body panels. Preferably the width of the crotch panel is not more than 100%, more preferably between 10 and 70% and most preferably between 20 and 40%, larger than the width of any of the front and back body panels.

In one embodiment illustrated in FIG. 2A, B the crotch panel 14 is a separate elastic web material attached to the elastic web material of the front and back body panels 12 and 13 along seams 26 and 27. The elastic web materials forming the front, back and crotch panels may be of the same or of different types. The difference in widths may be obtained by joining the elastic web materials to each other along the seams 26 and 27 in differently elongated condition, wherein the elastic web materials forming the front and back body panels are held in a more elongated condition than the elastic web material forming the crotch panel, which is held in a less elongated or in a relaxed condition. The elastic web materials forming the front and back body panels will upon relaxation retract more than the elastic web material forming the crotch panel, so that the different panels in a relaxed condition will have different widths as referred to above.

Figure 5A:
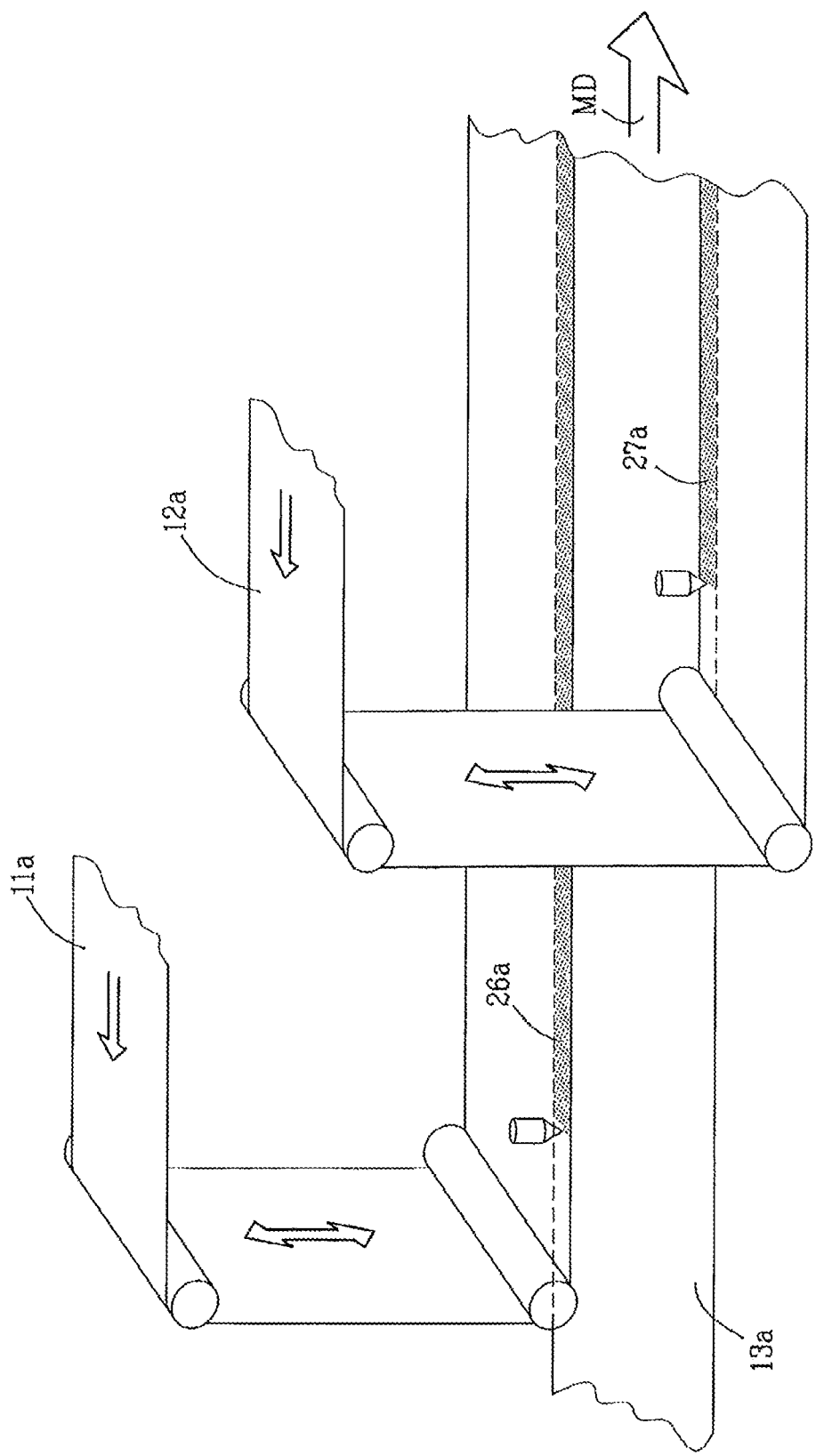
Figure 5B:
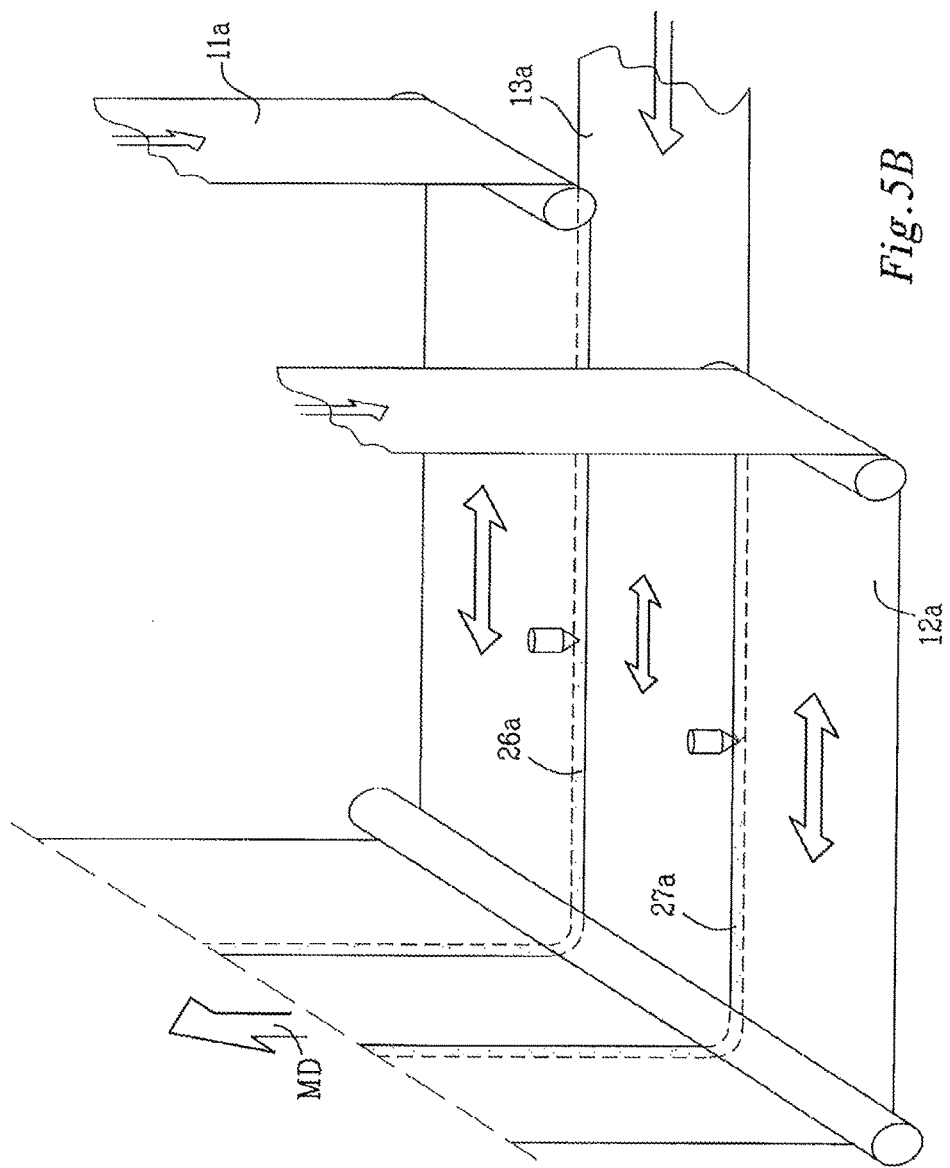

FIGS. 5A and 5B illustrate a process for joining elastic web materials 12a, 13a and 14a along seams 26a and 27a. The elastic web materials will form the front 12, back 13 and crotch panels. The elastic web materials 12a and 13a are held in a more elongated condition than the elastic web material 14a when being joined to each other. The elastic web materials 12a, 13a and 14a are preferably joined to each other at the same stage of the process, although for clarity reasons FIGS. 5A and 5B shows that they are joined at different stages of the process.

In another embodiment illustrated in FIG. 3 the crotch panel 14 is integral with the front and back body panels 12 and 13. In order to accomplish the desired increase of width of the crotch panel 14, it has been exerted to a treatment that will extend or deform it in a manner so that it will not completely recover its original retracted dimension. This extension or deformation should be at least in the transverse direction x of the pant article.

FIG. 6 illustrates a process for incremental stretching the centre part of an elastic web material 27 by means of rolls 28, 29 having intermeshing gears 30, 31 at its centre part, so that only the centre part of the elastic web material intended to form the crotch panel 14 is incrementally stretched and permanently deformed and extended.

Elasticity Test

The method measures how an elastic material behaves at repeated load and unload cycles. The sample is stretched to a predetermined elongation and a cyclic movement between 0 and said predetermined elongation is performed. Desired load and unload forces are recorded. The permanent, i.e. remaining, elongation of the relaxed material is measured.

A suitable tensile tester, such as Lloyd LRX, able to perform cyclic movements and equipped with a printer/plotter or software presentation is used. The sample is prepared by cutting it to a width of 25.4 mm and a length that is preferably 20 mm longer than the distance between the clamps in the tensile tester. Condition sample at a temperature of 23° C.±1° C. and 50% RH±5% RH before testing.

The tensile tester is calibrated according to the apparatus instructions. The parameters needed for the test (load and unload forces) are adjusted to:

Crosshead speed: 500 mm/min
Clamp distance: 50 mm
Preload: 0.05 N

The sample is placed in the clamps according to the markings made for the clamps and it is made sure that the sample is centred and fastened perpendicularly in the clamps. The tensile tester is started and three cycles between 0 and the predetermined elongation are performed. There is no pause between the first and second cycle. Before the last cycle, the sample is relaxed for 1 minute, then the permanent elongation is measured by stretching the sample until a force of 0.1 N is detected and the elongation is read.

The term elastic is used herein to define a material having a permanent elongation after relaxation of less than 10% after the material has been subjected to an elongation of 30% in the test above. An elongation of 30% means an elongation to a length that is 30% longer than the initial length of the sample.

The invention claimed is:

1. An absorbent pant article in the form of boxer shorts comprising:
   a garment shell including a front body panel, a back body panel, and a crotch panel positioned between the front and back body panels, an absorbent core arranged in at least the crotch panel, side seams connecting the front body panel to the back body panel, and a pair of leg openings and hanging legs, said article having a longitudinal direction and a transverse direction, wherein
   each of said front body panel, back body panel and crotch panel is made of elastic web material, the leg openings are located in the crotch panel and do not extend into the front and back body panels, and said side seams extend into the crotch panel, and the width of the crotch panel in a relaxed condition of the elastic web material, as measured in the transverse direction between the side seams of the article, is at least 7% larger than the width of any of the front and back body panels in a relaxed condition of the elastic web material of the front and back body panels, as measured between the side seams of the article, and
   the elastic web material in the crotch panel is a separate elastic web material attached to the elastic web material of the front and back body panels, and the elastic web material in the crotch panel is joined to the elastic web material in at least one of the front and back body panels while at least the elastic web material of said at least one of the front and back body panels is held in an elongated condition, and the elastic web material in the crotch panel is in a relaxed condition or in a less elongated condition as compared to the elastic web material in said at least one of the front and back body panels, or alternatively the elastic web material in the crotch panel is the same and integral with the elastic web material in the front and back body panels, and exhibits a quality of having been exerted to a treatment that has extended or deformed the elastic web material in the crotch panel in the transverse direction of the absorbent pant article so that the width of the crotch panel is larger than the width of any of the front and back body panels.

2. The absorbent pant article as claimed in claim 1, wherein the width of the crotch panel in the relaxed condition of the elastic web material, as measured between the side seams of the article, is at least 10% larger than the width of any of the front and back body panels in the relaxed condition of the elastic web material of the front and back body panels, as measured between the side seams of the article.

3. The absorbent pant article as claimed in claim 1, wherein the width of the crotch panel in the relaxed condition of the elastic web material, as measured between the side seams of the article, is not more than 100% larger than the width of any of the front and back body panels in the relaxed condition of the elastic web material of the front and back body panels, as measured between the side seams of the article.

4. The absorbent pant article as claimed in claim 1, wherein the width of the crotch panel in the relaxed condition of the elastic web material, as measured between the side seams of the article, is between 10 and 70% larger than the width of any of the front and back body panels in the relaxed condition of the elastic web material of the front and back body panels, as measured between the side seams of the article.

5. The absorbent pant article as in claim 1, wherein the elastic web material in the crotch panel is of the same type as the elastic web material in at least one of the front and back body panels.

6. The absorbent pant article as in claim 1, wherein the elastic web material in the crotch panel is of a different type than the elastic web material in at least one of the front and back body panels.

7. The absorbent pant article as in claim 1, wherein said side seams extend at least 10 mm into the crotch panel.

8. The absorbent pant article as in claim 1, wherein said elastic web material in the front, back and crotch panels is an elastic laminate comprising at least one fibrous layer and at least one film layer.

9. A method of making an absorbent pant article in the form of boxer shorts as claimed in claim 1, said method comprising the steps of:
   providing an elastic web material for forming said crotch panel, providing elastic web materials for forming said front and back body panels, attaching the elastic web material for forming the crotch panel to each of the web materials for forming the front and back body panels, at least one of elastic web materials for forming the front and back body panels being held in an elongated condition, and the elastic web material for forming the crotch panel being in a relaxed condition or in a less elongated condition as compared to at least one of the elastic web materials for forming the front and back body panels when the front and back panels are being attached to each other,
   providing leg openings in the web material forming the crotch panel,
   attaching an absorbent core to at least the web material for forming the crotch panel, and
   attaching the web materials for forming the front and back panels together to form said side seams, said side seams extending into the web material for forming the crotch panel.

10. The method as claimed in claim 9, wherein the web material for forming the crotch panel is of the same or different type as at least one of the web materials for forming the front and back panels.

11. A method of making an absorbent pant article in the form of boxer shorts as claimed in claim 1, said method comprising the steps of:
   providing an elastic web material for forming said front, back and crotch panels,
   exerting the elastic web material in an area that forms the crotch panel to a treatment that extends or deforms the elastic web material in a direction that forms the transverse direction of the absorbent pant, so that the elastic web material in the area that forms the crotch panel has a dimension exceeding the dimension of the elastic web material in areas that form the front and back body panels,
   providing leg openings in the area that forms the crotch panel,
   attaching an absorbent core to at least the area that forms the crotch panel, and attaching the areas of the elastic web material that form the front and back panel together to form said side seams, said side seams extending into the area that forms the crotch panel.

12. The absorbent pant article as claimed in claim 1 wherein the width of the crotch panel in the relaxed condition of the elastic web material, as measured between the side seams of the article, is between 20 and 40% larger than the width of any of the front and back body panels in the relaxed condition of the elastic web material of the front and back body panels, as measured between the side seams of the article.

13. The absorbent pant article as in claim 1, wherein said side seams extend at least 20 mm into the crotch panel.

14. The absorbent pant article as in claim 1, wherein the elastic web material in the crotch panel is the same and integral with the elastic web material in the front and back body panels, and exhibits a quality of having been exerted to a treatment that has extended or deformed the elastic web material in the crotch panel in the transverse direction of the absorbent pant article so that the width of the crotch panel is larger than the width of any of the front and back body panels.

\* \* \* \* \*